United States Patent
Ramsay et al.

(10) Patent No.: US 7,710,571 B2
(45) Date of Patent: May 4, 2010

(54) OPTICAL MEMBRANE FORMATION SYSTEM AND METHOD

(75) Inventors: Glen Ramsay, Lakewood, NJ (US); David Anafi, Wellington, FL (US)

(73) Assignee: Wyatt Technology Corporation, Santa Barbara, CA (US)

( * ) Notice: Subject to any disclaimer, the term of this patent is extended or adjusted under 35 U.S.C. 154(b) by 0 days.

(21) Appl. No.: 12/184,991

(22) Filed: Aug. 1, 2008

(65) Prior Publication Data

US 2009/0087554 A1    Apr. 2, 2009

Related U.S. Application Data

(62) Division of application No. 10/632,547, filed on Aug. 1, 2003, now Pat. No. 7,420,683.

(60) Provisional application No. 60/400,183, filed on Aug. 1, 2002.

(51) Int. Cl.
    *G01N 21/55* (2006.01)
(52) U.S. Cl. ............... 356/445; 356/244; 356/427; 356/426
(58) Field of Classification Search ........... 356/445, 356/244, 427, 426
    See application file for complete search history.

(56) References Cited

U.S. PATENT DOCUMENTS

| | | | |
|---|---|---|---|
| 5,341,215 A | 8/1994 | Seher | ............... 356/445 |
| 5,341,245 A | 8/1994 | Seher | |
| 5,521,702 A * | 5/1996 | Salamon et al. | ............... 356/244 |
| 5,991,488 A | 11/1999 | Salamon et al. | |
| 6,140,045 A | 10/2000 | Wohlstadter et al. | |
| 6,245,578 B1 * | 6/2001 | Molloy | ............... 356/427 |
| 6,627,461 B2 | 9/2003 | Chapman et al. | |
| 6,921,615 B2 | 7/2005 | Sreenivasan et al. | |
| 2003/0026466 A1 * | 2/2003 | Anderson et al. | ............... 382/129 |

* cited by examiner

Primary Examiner—Gregory J Toatley, Jr.
Assistant Examiner—Iyabo S Alli
(74) Attorney, Agent, or Firm—Hayes Soloway P.C.

(57) ABSTRACT

The invention relates to a spectroscopy system and improved membrane formation techniques. The system has at least one light source operable to generate a source beam and a prism having a rear surface. A support block is disposed on the rear surface of the prism. The support block is formed with at least one sample well having a center and defines a substantially vertical rear cell surface having a center. The source beam is aimed at the sample well. A syringe filled with a membrane solution and having a needle with a distal end disposed in front of the sample well. The distal end is aimed at a point above the center of the rear cell surface. The syringe is operable to eject a steady stream of membrane solution from the needle onto the circular rear cell surface thereby forming a membrane defining at least a portion of a layer under test. The membrane has a substantially uniform thickness that covers substantially the entire rear cell surface. A detector operable to detect light that is at least one of reflected and scattered by the layer under test.

12 Claims, 6 Drawing Sheets

Figure 6
(Side View)

Figure 7
(Top View)

OPTICAL MEMBRANE FORMATION SYSTEM AND METHOD

This application is a divisional of U.S. application Ser. No. 10/632,547, filed August 1, 2003, now U.S. Pat. No. 7,420,683, which in turn claims priority of U.S. Provisional Application 60/400,183, filed Aug. 1, 2002.

The invention relates to the field of membrane formation and in particular relates to the formation of optical membranes on optical surfaces such as prisms and the like. The invention is useful in connection with various spectroscopy techniques operable to characterize surface phenomenon including but not limited to: fluorescence microscopy systems, low angle neutron scattering systems, X-Ray scattering systems, surface plasmon resonance systems, plasmon-waveguide resonance systems and the like.

In the case of surface plasmon resonance systems, a light-reflecting surface is coated with a thin metallic coating. Light at a specific incident angle excites the electrons in the metal. This results in localized fluctuations of the electron density known as surface plasmons. The light energy transferred to the metal coating during excitation results in an attenuation of the reflected light intensity. The incident angle and degree of the attenuation depends on the wavelength of the exciting light and the thickness and optical properties of the interface in contact with the metal coating.

The important optical properties of such an interface include the absorbance at the excitation wavelength (extinction coefficient), the refractive index, and the thickness of the interface. The effective distance of Surface Plasmon penetration is only several hundred nanometers (nm) so only the environment at the surface is detected. This property makes Surface Plasmon Resonance (SPR) and Plasmon Waveguide Resonance (PWR) ideal for measuring surface and interfacial chemistry, as well as the properties of thin film coating properties (including molecular films). The formation of such films or membranes has previously been carried out manually. See e.g., U.S. Pat. No. 5,521,702—Salamon, et al., discussed below.

It is also understood that gold and silver are two metals that produce strong SPR signals. Under similar conditions the SPR electric field in the sample produced by silver is more than 2 times stronger than gold resulting in much sharper resonances and greater sensitivity. However, the chemical reactivity of silver renders it inappropriate for many applications. Therefore many applications utilize gold as the metallic coating.

PWR is essentially a species of SPR however, PWR techniques utilize one or more dielectric coatings (e.g., silica dioxide) over the metallic coating. The appropriate dielectric coatings serve as both a shield and an "optical amplifier". PWR allows the use of silver as the metallic coating or layer, with its improved optical properties but without suffering from its undesirable chemical properties.

SPR systems utilize specific light polarizations (e.g., p-polarization) in reference to the sample plane to produce resonance signals. In PWR systems, the appropriate dielectric coating also serves as an optical amplifier resulting in additional sharpening of the resonance spectrum, and more importantly, allowing light polarizations both parallel (s-polarization) and perpendicular (p-polarization) to the sample plane to produce resonance signals. For example, a silver layer 50 nm thick produces an SPR spectrum that is roughly 2 degrees wide.

The same layer when properly coated produces two different PWR spectra with the two light polarizations, that are more than an order of magnitude sharper. The unique characteristics of PWR allow more information about the sample properties to be obtained at much higher sensitivities. In particular, probing optically anisotropic samples requires the capabilities that PWR offers. Thus, for anisotropic samples, the refractive index and extinction coefficient have different values for polarizations parallel and perpendicular to the sample plane, yielding information about molecular orientation within the sample.

See e.g., U.S. Pat. No. 5,521,702—Salamon, et al.—which discloses the use and formation of a biocompatible film composed of a self-assembled bilayer membrane deposited on a planar surface in connection with SPR techniques. See also, U.S. Pat. No. 5,991,488—Salamon, et al. which discloses a prism having a metallic film coated with a dielectric layer used to provide a surface plasmon wave.

Most SPR instruments do not record the SPR spectra but reduce the information to only the relative angle at which the resonance peak is detected. This approach eliminates the possibility of determining optical properties. Changes in the relative angle are assumed to correlate to changes in the refractive index of the sample layer (measured with only one polarization) due to mass moving into and out of the layer. For this to be true, it is assumed that the sample is isotropic and that the thickness and absorbance (or scattering) are constant. Unfortunately these assumptions are not always correct in practical applications and can result in misleading data and erroneous conclusions. In addition, the molecular interactions resulting in changes in mass of the sample also usually influence the molecular organization. As an example, conformation changes occurring without net binding will result in changes in the relative angle. Further, changes in the bulk solvent will produce changes in the relative angle and can appear as binding effects. One way to avoid such misleading measurements is to use both polarizations and to analyze the full resonance spectrum.

There are a number of applications for a PWR spectrometer. For example, PWR devices can be used to probe molecular interactions (i.e. binding followed by structural alterations induced by binding) within anisotropic interfaces and thin films, including optical coatings, lipid bilayers, proteins and peptides inserted into lipid bilayers, and others. It can also be used the way as a conventional SPR instrument to follow changes in the angular resonance peak position.

The invention is directed to improvements in membrane formation techniques as well as improvements in automation techniques.

DETAILED DESCRIPTION OF THE INVENTION

Figure 1:
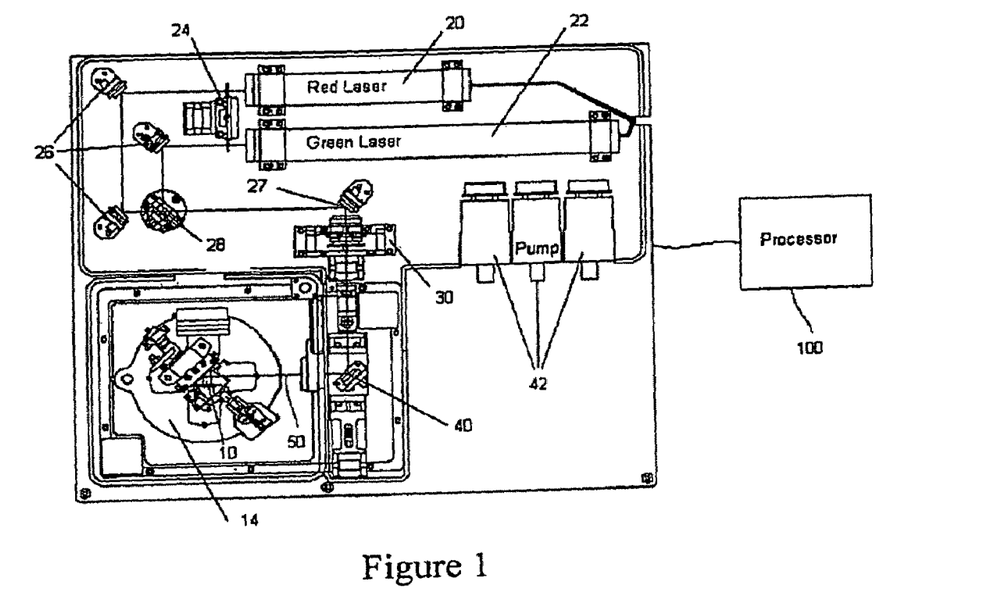
FIG. 1 is a pictorial view of a PWR device for use in accordance with the invention.

FIG. 1 shows a pictorial view of a surface plasmon resonance device used in connection with the invention. The device includes an optical element with an optical surface upon which a membrane will ultimately be formed. In this example, the optical element is a prism 10 having an optical surface at least partially coated with thin metallic coating. For PWR applications, the prism also includes a dielectric coating at least partially covering the metallic coating. It is understood that various optical elements including but not limited to prisms, mirrors, lenses and optical fibers are compatible with the invention.

A sample well is formed generally adjacent to the optical surface (in this example, the coated surface of the prism). The sample well generally supports a layer under test, for example a sample layer 12 (see FIG. 5). A layer under test can include one or more individual layers (e.g., self-assembled bilayer membrane). The invention is primarily directed towards systems and methods for forming an appropriate membrane on an optical surface (in this example the rear surface of a prism in a SPR or PWR system).

The layer under test generally forms a test plane that is generally adjacent and parallel to the coated surface of the prism. The prism is mounted to a turntable 14 having an axis of rotation. The device also includes a light source that is generally directed towards a surface of the prism and a detector 18 (see FIG. 2) that detects reflected and/or scattered light. In a basic mode of operation, a sample layer is formed in the sample well and at least a portion of the sample layer is illuminated via the light source. The turntable is rotated and a resonance peak is detected by the detector. The selected angle between the rear surface of the prism and the intensity of the reflected incident light beam is recorded and is generally correlated with changes in the refractive index, thickness and light absorption of the layer or sample under test.

Referring to FIG. 1, exemplary light sources include red and green lasers 20, 22, operable to generate red and green laser beams. Chopper 24 is operable to select one or both laser beams from lasers 20, 22. Mirrors 26 direct the selected laser beam sources towards beam combiner 28. The resultant red, green or mixed (e.g., orange) light is then directed towards mirror 27 and then polarizer 30 such that an appropriate polarizer is optionally selectable (e.g., linear polarizer—vertical or horizontal). It is understood that a broad range of light wavelengths can be used (e.g., ultraviolet, infrared etc).

The light beam is then directed towards a beam splitter which divides the light beam into essentially two portions. The first portion of the light beam is directed towards a reference detector. The second portion of the light beam (i.e., source beam) is directed towards a mirror 40 and finally the source beam is directed towards the prism 10. One or more pumps 42 with associated actuators, syringes and electronics are provided as discussed in more detail below.

Preferably, various system components (e.g., turntable, pumps and the like) are coupled to processor 100, operable to automate various system functions as discussed below. Processor 100 can be implemented using a typical personal computer and associated operating system such as a Microsoft Windows product, Linux or the like. The hardware and software configuration of a processor operable to control and automate a PWR device in accordance with the invention based on the disclosure herein is well within the grasp of those skilled in the art.

The term "light source" as recited herein refers to source of light in its broadest sense. It is understood that a variety of different light sources can be used to produce a suitable light beam, including but not limited to, semiconductor lasers, gas lasers, solid state lasers and the like. It is also understood that a light source can include various intermediate devices, including but not limited to, optical fibers, lenses and/or mirrors for focusing, collimating, polarizing, filtering, aiming and/or altering the properties of the light beam. Accordingly, the term "light source" as recited herein is not limited to the precise arrangement shown in FIG. 1.

Figure 2:
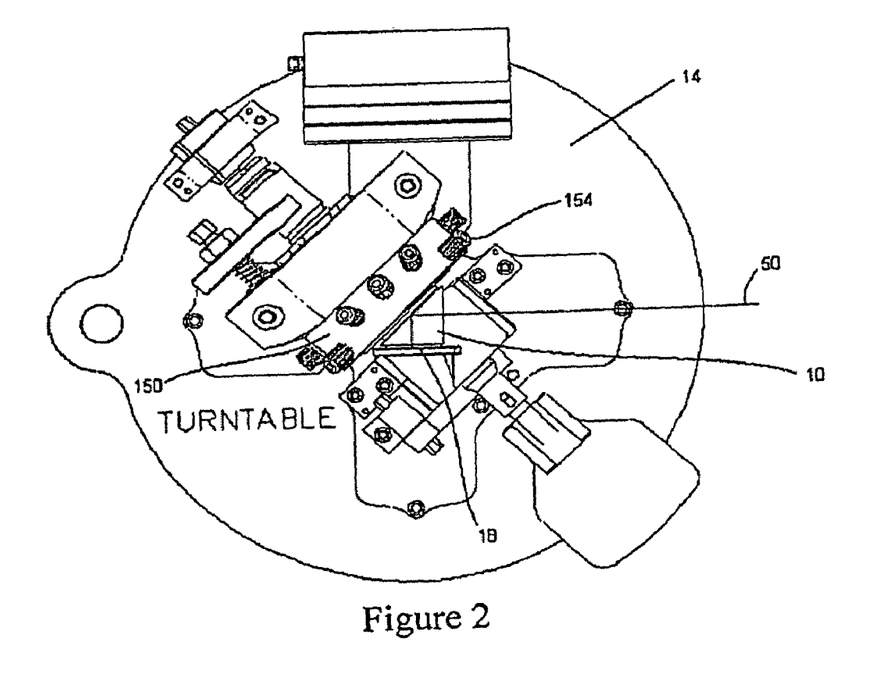
FIG. 2 is a pictorial view showing a more detailed view of a turntable, support block and prism in accordance with FIG. 1.

FIG. 2 shows a more detailed view of the turntable 14 and prism 10. As discussed above, turntable 14 has an axis generally located in the center of the turntable. Preferably, turntable 14 is coupled to a rotary drive mechanism (not shown) operable to automate rotary movement. Preferably, the rotary drive mechanism is coupled to a controller and/or processor (see e.g., FIG. 1—processor 100) operable to initiate rotary movement of the turntable and track the angle of the turntable with respect to the source beam. The tracking of selected angles, interconnection of turntables, rotary drive mechanisms and controllers and/or processors based on the disclosure herein is well within the grasp of those skilled in the art.

Figure 3:
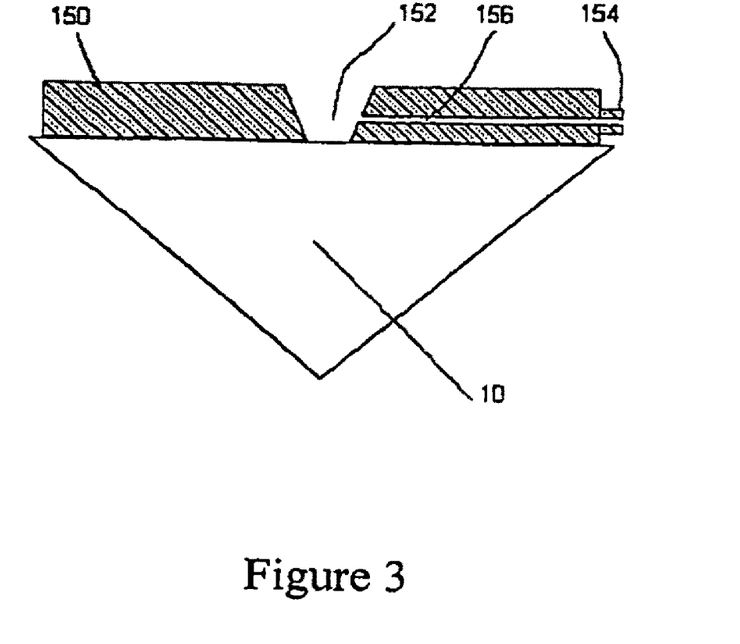
FIG. 3 is a pictorial view showing a more detailed view of the prism, support block, sample well, ports and passages in accordance with FIG. 2.

Referring to FIGS. 2 and 3, a support block 150 is generally pressed against the rear surface of the prism. The support block is generally formed with at least one sample well 152 (see FIG. 3). The support block is also preferably formed with one or more ports 154 each having at least one associated passage 156 (see FIG. 3). The ports 154 and passages 156 are generally utilized to carry fluids (e.g., liquids or gasses) to and/or from the sample well 152, as discussed on more detail below. Support block 150 can be fabricated from a variety of materials. In the current example, the support block is preferably formed from PTFE (e.g., TEFLON®).

FIG. 3 shows only a sectional view of the support block 150, a single sample well 152 and a single port 154 with one associated passage 156. It is also understood that a plurality of ports can be provided, each having one or more passages. It is understood that the sample block can be formed with a plurality of sample wells, each having one or more associated ports and passages. In the current example, the rear surface of the prism is disposed generally vertically. Accordingly, gravitational forces must be taken into account with respect to the various port locations. For example, ports intended to deliver fluids to the sample well can have an opening located in the upper portion of the sample well. Ports intended to remove fluids from the sample well can have an opening located in the lower portion of the sample well.

Figure 4:
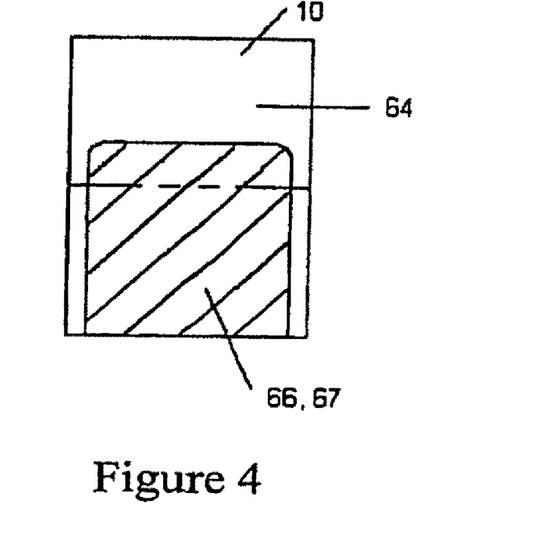
FIG. 4 is a pictorial view showing an exemplary prism structure for use in accordance with the invention.
Figure 5:
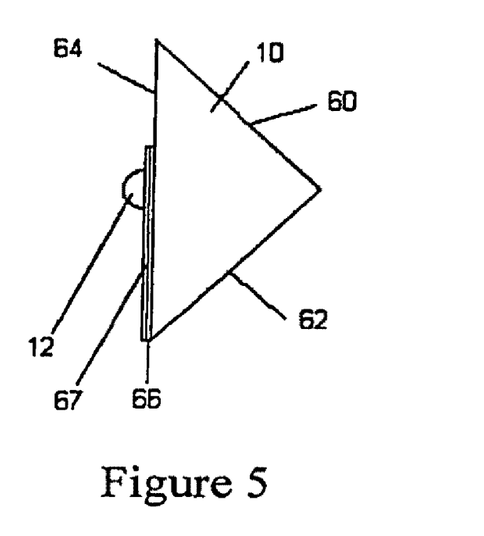
FIG. 5 is a pictorial view showing the prism structure of FIG. 4 and a sample layer in accordance with the invention.

FIGS. 4 and 5 show an exemplary prism structure for use in accordance with the invention. The support block has been omitted for purposes of clarity. Sample layer 12 is shown generally located on the center of the rear surface of the prism. It is understood that sample layer 12 can be formed on any portion of the rear prism surface. It is also understood that in the current example, sample layer 12 is at least partially surrounded by a sample well formed in an associated support block.

The prism 10 has an entrance surface 60, an exit surface 62 and a rear surface 64. In the current example, the rear surface of the prism is at least partially coated with a metallic film 66. In the case of PWR applications, the prism is optionally coated with a dielectric layer 67 (e.g., silica dioxide). As discussed above, the two metals that produce the strongest SPR signals are gold and silver. Since PWR techniques include a dielectric layer, silver is preferable. However, other metallic layers are compatible with the invention.

Membrane Formation

Figure 6:
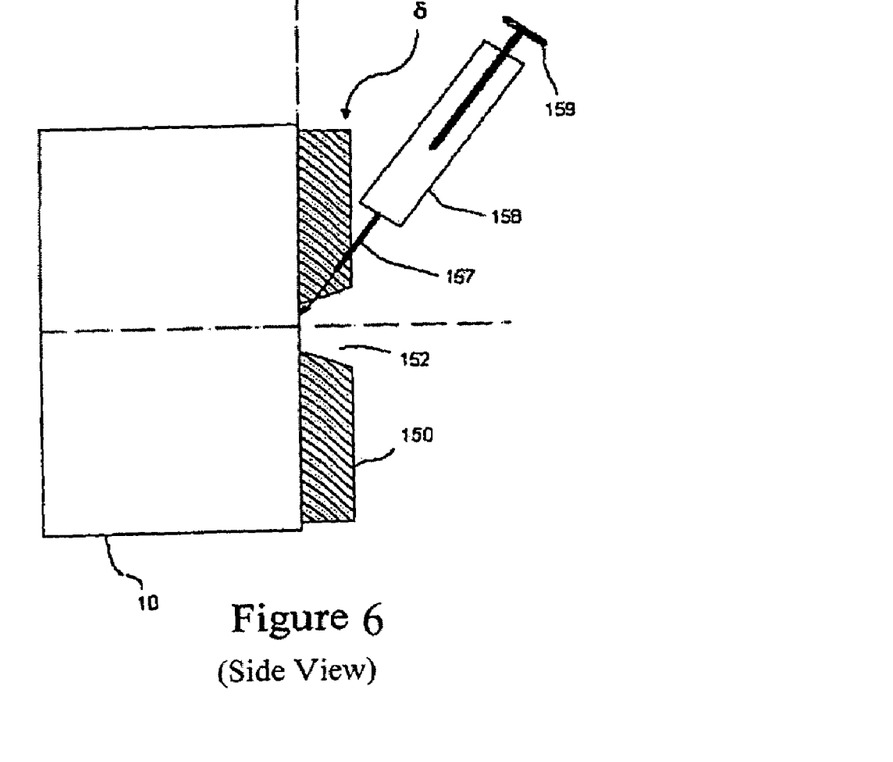
FIG. 6 is a top view pictorial diagram showing the aiming of a syringe used to form a membrane in accordance with the invention.
Figure 7:
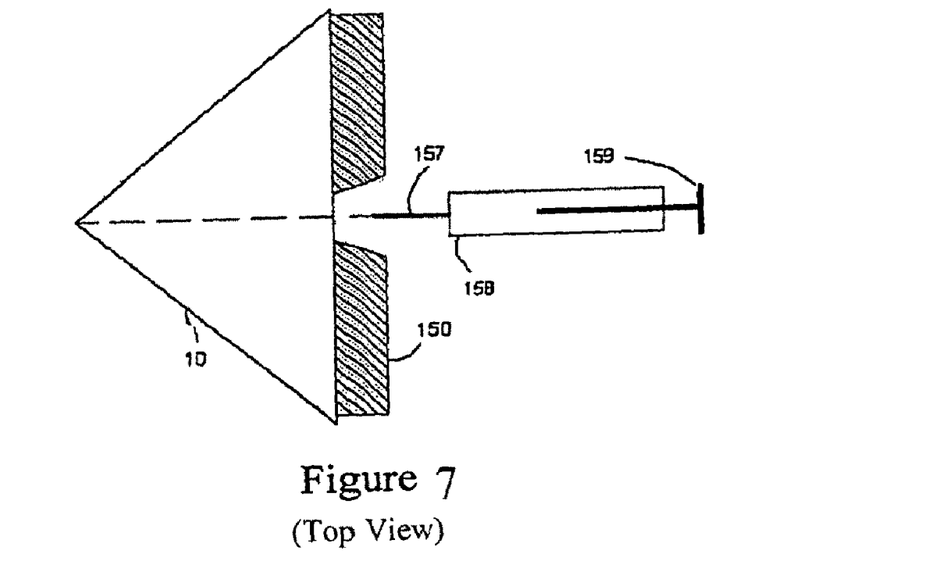
FIG. 7 is a side view pictorial diagram showing the aiming of a syringe used to form a membrane in accordance with the invention.

FIGS. 6 and 7 show the relationship between a syringe and the sample well and the rear surface of the prism during membrane formation. The support block is shown in sectional form. The sample well 152 is generally circular in cross section, thereby defining an open cell with PTFE walls and a generally vertically disposed circular rear cell surface (i.e., the rear surface of the prism). The PTFE walls are generally sloped as shown in FIGS. 3, 6 and 7. It is understood that various geometric profiles and surface textures can be used without departing from the invention. The membrane will be formed between the PTFE walls and will rest on the rear cell surface (i.e., on the rear surface of the prism—over the metal film and/or dielectric if such layers are present).

In this example, the diameter of the circular rear cell surface is approximately 5 mm. The syringe 158 volume is 10 microliters and is fitted with a 0.13 mm needle (inside diameter). Syringe 158 is filled with a suitable membrane solution (e.g., egg phosphatidlcholine in squalene and butanol). Syringe 158 is generally positioned in front of the cell and the needle 157 is aimed approximately 1 mm above the center of the cell. It is understood that the syringe can be supported by a variety of different structures. In this example, the syringe is disposed at an angle δ with respect to the rear surface of the prism. In the current example, δ is in the 20°-40° range.

Figure 8:
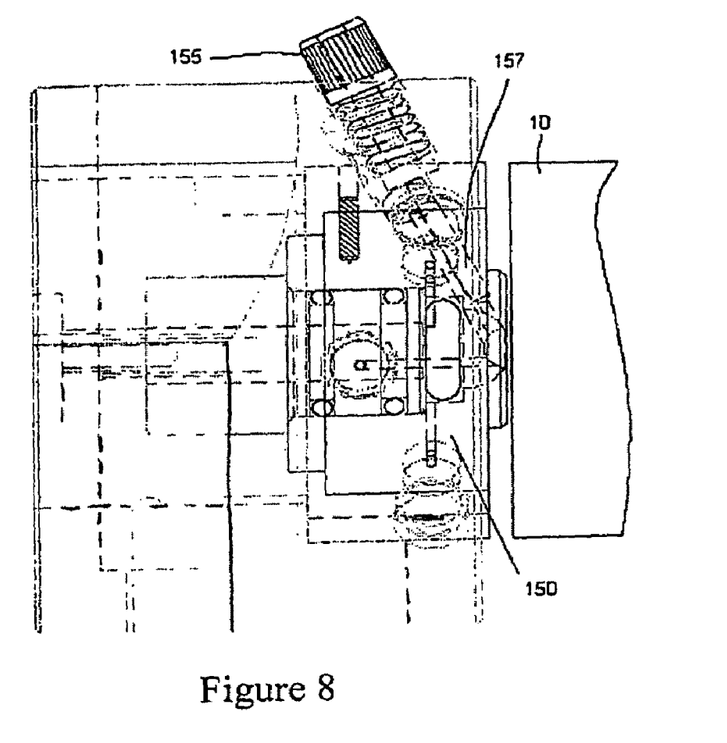
FIG. 8 is a pictorial view of a support block for supporting a needle in accordance with the invention.
Figure 9:
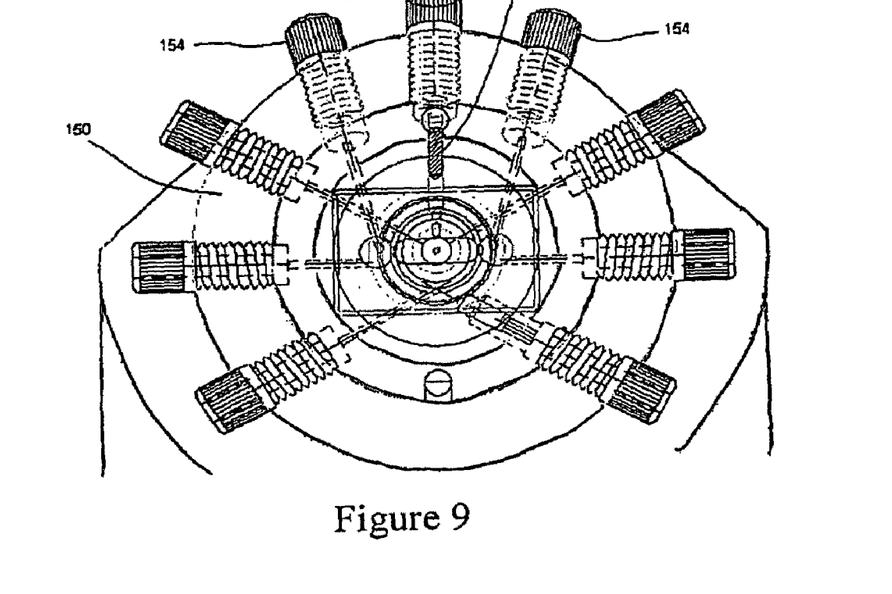
FIG. 9 is a pictorial view of a support block for supporting a needle in accordance with the invention.

FIGS. 6 and 7 show a syringe 158 with a needle coupled directly to the syringe body. It is understood that intervening structures such as conduits or tubing can be used to couple the needle and syringe body in fluid communication. To this end, FIGS. 8 and 9 show an exemplary support block 150 with a membrane formation port 155 operable to position and aim a needle appropriately. The port is coupled to the syringe via a conduit (not shown). It is understood that the term syringe herein encompasses a variety of structures operable to dispense a metered quantity of fluid without departing from the scope of the invention.

The plunger 159 is rapidly depressed such that a steady stream of membrane solution is ejected from the needle and strikes the circular rear surface of the cell. A membrane is formed on the rear cell surface. It is understood that syringe 158 can be coupled to a suitable pump (e.g., one of pumps 42 shown in FIG. 1) so that membrane formation can be initiated under processor control.

The membrane has a substantially uniform thickness and covers the entire rear cell surface. Coverage of the rear cell surface is difficult to achieve because the membrane solution is hydrophobic and will preferentially interact with the hydrophobic PTFE walls of the support block 150. When the membrane solution is injected on the rear cell surface (e.g., coated rear surface of the prism) it should spread uniformly to make contact with the PTFE at the perimeter of the available coated surface. When the coated rear surface is in a vertical position the initial contact point of the membrane solution must be above the center point of the coated rear surface (as described by the circular opening in the PTFE support block) to offset the effect of gravity.

The invention is advantageous in that a membrane is created on an optical surface while it is located in the operating position of the instrument or system. This aids in maintaining the position of the surface relative to the other instrument components to a tight tolerance (e.g., better than millidegrees of rotation). Prior to the invention, the formation of such a membrane required disassembly of the apparatus for manual application of the membrane solution. See e.g., U.S. Pat. No. 5,521,702—Salamon et al. The invention is also advantageous in that the membrane formation as well as other system functions can be automated.

Figure 10:
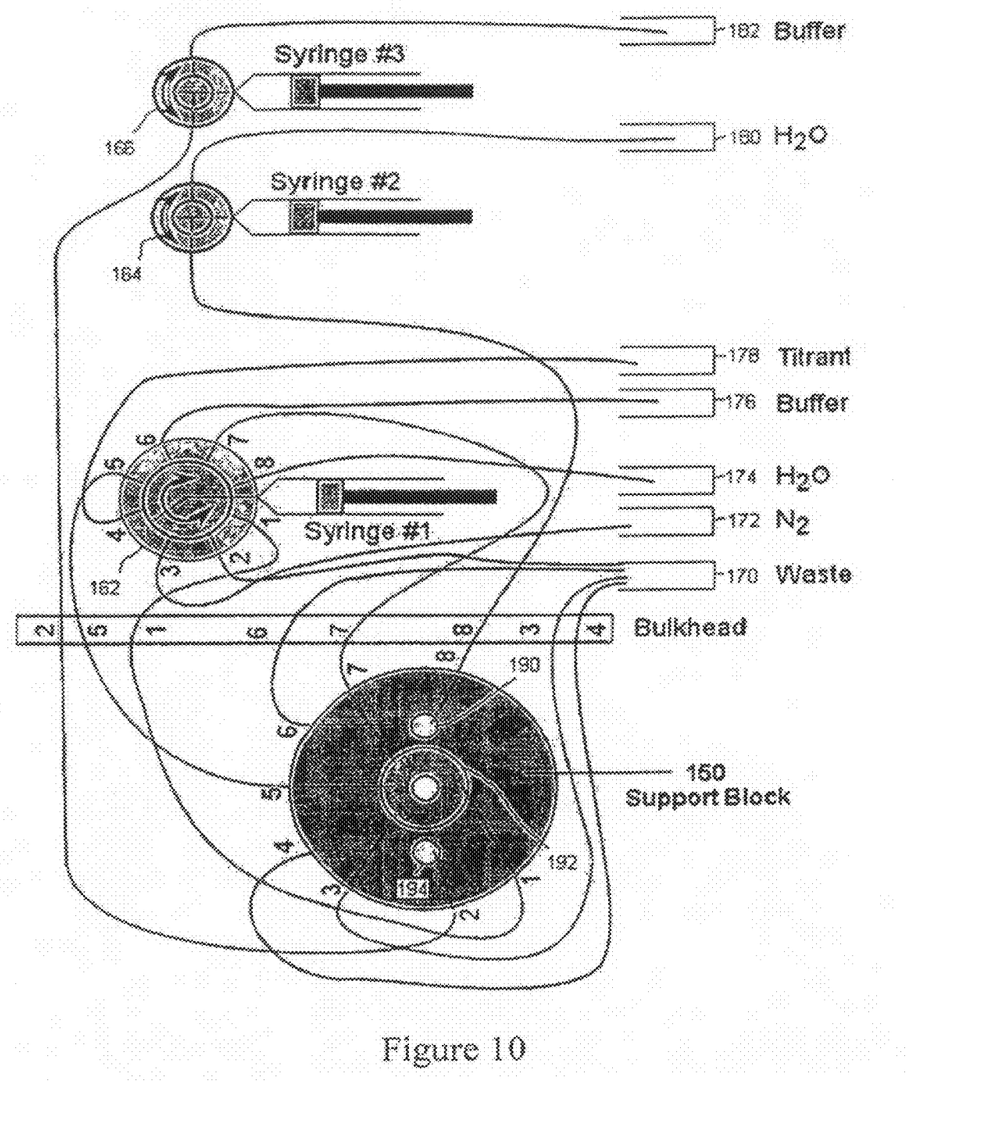
FIG. 10 is an exemplary diagram showing the interconnection of various system components in accordance with the invention.

To this end, FIG. 10 is an exemplary diagram showing the interconnection of various system components. Syringe #1, Syringe #2 and Syringe #3 are coupled to pumps 42 (FIG. 1) and are generally operable to dispense a metered quantity of fluid. Pumps 42 generally include a syringe support and a linear slide that engages with the syringe plunger. The linear slide and associated actuator that are preferably coupled to a processor (e.g., processor 100). The hardware and software configuration of a processor operable to control and automate a pump in accordance with the invention based on the disclosure herein is well within the grasp of those skilled in the art.

Syringe #1, syringe #2 and syringe #3 are coupled to valves 162, 164 and 166 via conduits. Valve 162 is an 8 way valve operable to couple syringe #1 to a plurality of different reservoirs (e.g., 170-Waste, 172-$N_2$, 174 $H_2O$, 176-Buffer and 178 Titrant). Valves 164 and 166 are typical three way L port valves. Valve 164 is operable to selectively couple syringe #2 to either reservoir 180 ($H_2O$) or port #8 on the support block 150. Valve 166 is operable to selectively couple syringe #3 to either reservoir 182 (buffer) or port #2 support block 150.

Example

Running a Lipid PWR Experiment

In this example, the support block is formed with three sample wells and the rear surface of the prism is partially coated with a metallic coating, thereby defining a coated portion and an uncoated portion. A first sample well 190 is located on an uncoated portion of the prism (bare reference position). A second sample well 192 is located on a coated portion of the prism (sample position). A third sample well 194 is also located on a coated portion of the prism (coated reference position). The device is generally operable to direct the light source 50 towards any of the sample wells under processor control. The structures required to shift the source beam to the desired position on the rear surface of the prism are disclosed in a U.S. patent application Ser. No. 10/632,547 filed Jul. 26, 2002, entitled "Beam Shifting Surface Plasmon Resonance System and Method" herein incorporated by reference in its entirety. It is also understood that all of the various system components can be coupled to a processor operable to initiate and coordinate operation of the components (e.g., operation of valves, extraction of fluids from reservoirs and delivery of fluids to the sample well).

The following is an example of how an experiment can be conducted using the disclosed system.

1. Turn on instrument and software to start warming up.
2. Clean support block 150 and prism 10 and tubing.
3. Prepare lipid and buffer:
    A. 8 mg/ml egg PC dissolved in squalene/butanol (0.007: 0.993; v/v)
        i. Open one 50 mg vial after tapping lipid into bottom.

ii. Add to vial 6.21 ml of butanol and 44 µl of squalene.
iii. Mix until lipid is dissolved, transfer to screw capped tube.
B. 10 mM TRIS, 10 mM KCl, 0.5 mM EDTA
   i. 154.6 mg TRIZMA HCl
   ii. 75 mg KCl
   iii. 19 mg Disodium EDTA
   iv. Mix in 100 ml of DI water and adjust to pH 7.3
4. Assemble block, prism and tubing.
5. Calibrate Baseline with Air as the reference at the Bare Reference Position.
6. Fill Sample and Bare Reference Positions with fresh pure Water:
   A. Using valve 1 to fill Sample, lines 5 and 7, then fill line 1 until no bubbles come out line 3.
   B. Use valve 2 to fill Bare Reference until no bubbles come out.
7. Calibrate Angle with Water as the reference at the Bare Reference Position.
8. Take Water spectra at the Sample Position over the 60 to 70 degree range:
   A. Red P
   B. Red S
   C. Green S
   D. Green P
9. Fill Sample lines 5 and 7 with air, drain line 1 to waste.
10. Dry lines 5, 7 and 1 with nitrogen, exiting through line 3.
11. Remove line 5 and inject 1.5 µl of lipid.
12. Fill Sample and Bare Reference Positions with fresh buffer:
   A. Using Syringe and Valve 162 to fill Sample Position, lines 5 and 7, then fill line 1 until no bubbles come out line 3.
   B. Use Syringe and Valve 2 to fill Bare Reference Position until no bubbles come out.
13. Take the Red S spectrum at the Sample Position for initial conditions.
14. Take Buffer TIR spectra at Bare Reference Position:
   A. Red P
   B. Red S
   C. Green P
   D. Green S
15. Repeatedly take Red S spectra at Sample Position at 10 minute intervals to monitor development of the lipid bilayer. Move to next step after spectra are stable. Stability is defined as 0 degree change over ½ hour.
16. Take Lipid spectra at the Sample Position over the 60 to 70 degree range:
   A. Red P
   B. Red S
   C. Green P
   D. Green S
17. The final Red S spectrum at the Sample Position over the range of 60 to 70 degrees to confirm stability of sample.
18. Flush lines with water, then dry with nitrogen.
19. Remove and clean Teflon block and prism.

Figure 11:
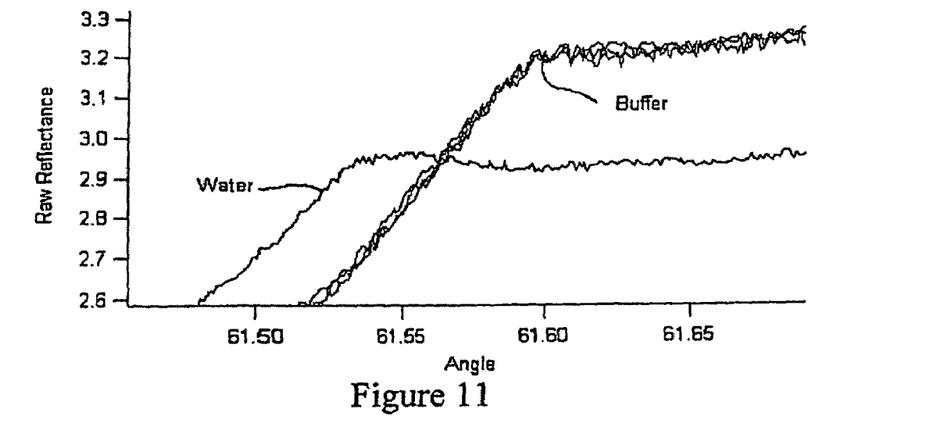
FIG. 11 is a graph showing exemplary graph of raw reflectance plotted against selected angle for two different layers under test in accordance with the invention.
Figure 12:
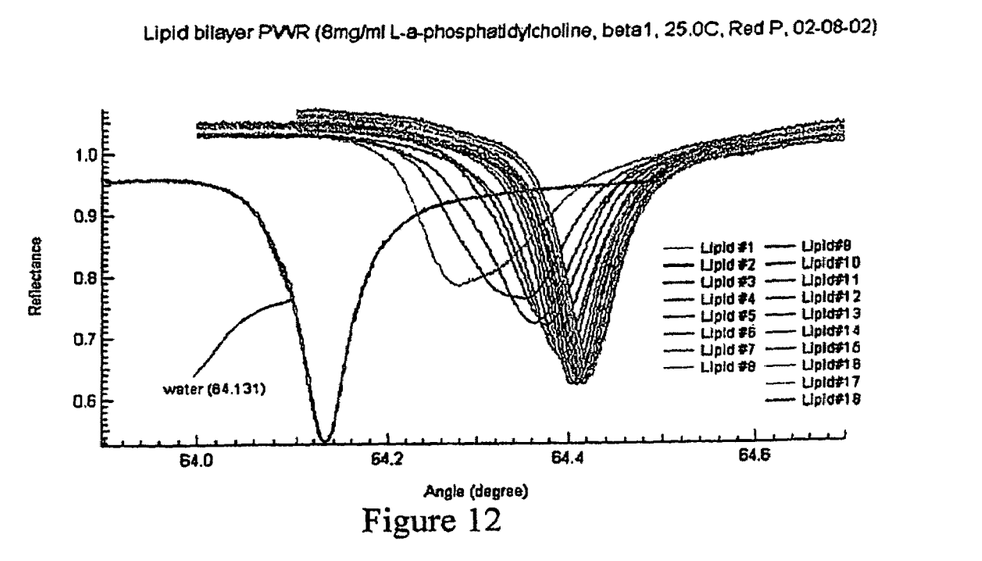
FIG. 12 is a graph showing exemplary graph of reflectance plotted against selected angle for various layers under test in accordance with the invention.

FIG. 11 is an exemplary graph produced in accordance with the invention. In this example, raw reflectance of bare reference is plotted against the selected angle for two different layers under test (water and a buffer). FIG. 12 is yet another is an exemplary graph produced in accordance with the invention. In this example, reflectance of the sample position is plotted against the selected angle for various layers under test. The left most curve (water) shows a null at approximately 64.131°. The remaining curves (various lipid bilayers) have nulls that falling approximately in the 64.26° to 64.42° range. The results shown in FIGS. 11 and 12 generally illustrate the level of precision that is realized utilizing the structures and methods disclosed herein. A more detailed analysis of these graphs is beyond the scope of this disclosure.

While this invention has been described with an emphasis upon preferred embodiments, it will be obvious to those of ordinary skill in the art that variations in the preferred devices and methods may be used and that it is intended that the invention may be practiced otherwise than as specifically described herein.

What is claimed is:

1. A method of forming a membrane in a spectroscopy system having an operating position comprising:
   providing an optical element having an optical surface,
   providing a support block formed with at least one sample well having a center, the support block being disposed on the optical surface thereby defining a substantially vertical rear cell surface having a center,
   providing a syringe filled with a membrane solution in fluid communication with a needle having a distal end disposed in front of the sample well,
   aiming the distal end at a point above the center, in a vertical direction, of the rear cell surface,
   ejecting a steady stream of membrane solution from the needle onto the circular rear cell surface thereby forming a membrane defining at least a portion of a layer under test, the membrane having a substantially uniform thickness that covers substantially the entire rear cell surface, wherein the membrane is formed on the optical surface while the optical surface is located in the operating position of the spectroscopy system.

2. The method of claim 1 comprising:
   providing at least one actuator coupled to the syringe and a processor coupled to the actuator wherein the processor is operable to initiate the formation of the membrane.

3. The method of claim 1 wherein the optical element is at least one of a prism, mirror, lens and optical fiber.

4. The method of claim 3 wherein optical surface is at least partially coated with a metallic coating.

5. The method of claim 3 wherein the metallic coating is at least partially coated a dielectric layer.

6. The method of claim 1 comprising:
   providing a plurality of syringes each having at least one associated actuator and a processor coupled to the actuators wherein the processor is operable to initiate the delivery of fluids to the sample well.

7. The method of claim 1, comprising
   providing a plurality of syringes each connected to a different supply reservoir.

8. The method of claim 7, wherein one of the supply reservoirs is a wash solution.

9. The method of claim 1, wherein the support block comprises three sample wells.

10. The method of claim 9, wherein the optical surface includes coated and uncoated portions, and one of the sample wells is located on an uncoated portion of the optical surface.

11. The method of claim 9, wherein the optional surface includes coated and uncoated portions, and one of the sample wells is located on a coated portion of the optical surface.

12. The method of claim 1, wherein the support block includes a port that is coupled to the syringe, wherein said port is configured to deliver and/or remove fluids from the sample well.

* * * * *